United States Patent
Tahmasebi Maraghoosh et al.

(10) Patent No.: US 11,361,530 B2
(45) Date of Patent: Jun. 14, 2022

(54) SYSTEM AND METHOD FOR AUTOMATIC DETECTION OF KEY IMAGES

(71) Applicant: KONINKLIJKE PHILIPS N.V., Eindhoven (NL)

(72) Inventors: Amir Mohammad Tahmasebi Maraghoosh, Arlington, MA (US); Thusitha Dananjaya De Silva Mabotuwana, Bothel, WA (US); Yuechen Qian, Lexington, MA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 119 days.

(21) Appl. No.: 16/314,104

(22) PCT Filed: Jun. 22, 2017

(86) PCT No.: PCT/EP2017/065347
§ 371 (c)(1),
(2) Date: Dec. 28, 2018

(87) PCT Pub. No.: WO2018/001847
PCT Pub. Date: Jan. 4, 2018

(65) Prior Publication Data
US 2019/0325249 A1     Oct. 24, 2019

Related U.S. Application Data

(60) Provisional application No. 62/355,411, filed on Jun. 28, 2016.

(51) Int. Cl.
*G06V 10/44* (2022.01)
*G16H 30/20* (2018.01)
(Continued)

(52) U.S. Cl.
CPC ............ *G06V 10/44* (2022.01); *G06T 7/0012* (2013.01); *G06T 17/10* (2013.01); *G16H 30/20* (2018.01);
(Continued)

(58) Field of Classification Search
CPC ...... G06K 9/4604; G16H 30/20; G16H 30/40; G06T 7/0012; G06T 17/10; G06T 2207/30096; G06V 10/44
See application file for complete search history.

(56) References Cited

U.S. PATENT DOCUMENTS 8,139,834 B2 * 3/2012 Khorasani .............. A61B 6/502
382/128
8,935,155 B2   1/2015 Bretschneider
(Continued)

OTHER PUBLICATIONS

Shin Hoo-Chang et al., "Interleaved text/image Deep Mining on a large-scale radiology database", 2015 IEEE Conference on Computer Vision and Pattern Recognition (CVPR), IEEE, Jun. 7, 2015, pp. 1090-1099.

*Primary Examiner* — Shefali D Goradia (57) ABSTRACT

A radiology workstation (10) includes a computer (12) connected to receive a stack of radiology images of a portion of a radiology examination subject. The computer includes at least one display component (14) and at least one user input component (16). The computer includes at least one processor (22) programmed to: display selected radiology images of the stack of radiology images on the at least one display component; receive entry of a current radiology report via the at least one user input component and displaying the entered radiology report on the at least one display component; identify a radiology finding by at least one of (i) automated analysis of the stack of radiology images and (ii) detecting textual description of the radiology finding in the radiology report; identify or extract at least one (Continued)

key image from the stack of radiology images depicting the radiology finding; and embed or link the at least one key image with the radiology report.

15 Claims, 3 Drawing Sheets

(51) Int. Cl.
   *G16H 30/40* (2018.01)
   *G06T 7/00* (2017.01)
   *G06T 17/10* (2006.01)
(52) U.S. Cl.
   CPC ... *G16H 30/40* (2018.01); *G06T 2207/30096* (2013.01)

(56) References Cited

U.S. PATENT DOCUMENTS

| | | | |
|---|---|---|---|
| 9,081,877 | B2 | 7/2015 | Futami et al. |
| 9,904,966 | B2 * | 2/2018 | Mabotuwana ......... G06Q 10/10 |
| 10,657,220 | B2 * | 5/2020 | Roberge ................ G16H 15/00 |
| 2009/0087067 | A1 * | 4/2009 | Khorasani ............. A61B 6/502 382/132 |
| 2009/0309874 | A1 * | 12/2009 | Salganicoff ............ G06T 19/00 345/419 |
| 2014/0006926 | A1 | 1/2014 | Yeluri et al. |
| 2014/0257854 | A1 * | 9/2014 | Becker ................. G06F 19/321 705/3 |
| 2014/0278554 | A1 | 9/2014 | Mabotuwana et al. |
| 2016/0314278 | A1 * | 10/2016 | Mabotuwana ........ G06F 40/279 |

* cited by examiner

SYSTEM AND METHOD FOR AUTOMATIC DETECTION OF KEY IMAGES

CROSS-REFERENCE TO PRIOR APPLICATIONS

This application is the U.S. National Phase application under 35 U.S.C. § 371 of International Application No. PCT/EP2017/065347, filed on Jun. 22, 2017, which claims the benefit of U.S. Patent Application No. 62/355,411, filed on Jun. 28, 2016. These applications are hereby incorporated by reference herein.

FIELD

The following relates to the radiology arts, radiology reporting arts, medical imaging arts, and related arts.

BACKGROUND

In imaging modalities such as computed tomography (CT), magnetic resonance imaging (MRI), positron emission tomography (PET), or so forth, the imaging commonly produces a stack of radiology images, which are sometimes referred to as image slices. In a common orientation, the patient lies in a prone or supine position, the image slices are transverse to the axial direction (running head-to-toe) of the patient, and the stack of radiology images is thus a stack of axial images. A typical radiology reporting workflow involves the radiologist looking through the radiology images of the stack of radiology images acquired in an imaging study, identifying a radiology image of the stack which best depicts a finding for a tumor, lesion, or other feature of clinical interest, and dictating a narrative report describing the observed radiology findings. A snapshot of a reference image chosen by the radiology may be saved on a Picture Archiving and Communication System (PACS) as the key image for future reference. However, typically, there is no association between the findings described in the written radiology report and the image(s) the findings were observed on. Further, due to time constraints the radiologist may not make a careful selection of the reference image. This makes it difficult for the downstream consumers of the reports (e.g., referring physicians) to navigate to the images where the radiologist observed the findings and match them with the descriptions in the report.

Sometimes the specific finding may correspond to visualization that spans through several slices and therefore, it may not be obvious to the radiologist which is the most appropriate image slice to be considered as the key image to match the finding. Further, there is inherent user variability, resulting in various inconsistencies.

The following provides new and improved devices and methods which overcome the foregoing problems and others.

BRIEF SUMMARY

In accordance with one aspect, a radiology workstation includes a computer connected to receive a stack of radiology images of a portion of a radiology examination subject. The computer includes at least one display component and at least one user input component. The computer includes at least one processor programmed to: display selected radiology images of the stack of radiology images on the at least one display component; receive entry of a current radiology report via the at least one user input component and displaying the entered radiology report on the at least one display component; identify a radiology finding by at least one of (i) automated analysis of the stack of radiology images and (ii) detecting textual description of the radiology finding in the radiology report; identify or extract at least one key image from the stack of radiology images depicting the radiology finding; and embed or link the at least one key image with the radiology report.

In accordance with another aspect, a radiology workstation includes a computer connected to receive a stack of radiology images of a portion of a radiology examination subject. The computer includes at least one display component and at least one user input component. The computer includes at least one processor programmed to: display selected radiology images of the stack of radiology images on the at least one display component; receive entry of a current radiology report via the at least one user input component and display the entered radiology report on the at least one display component; convert the stack of radiology images to a three-dimensional (3D) image; identify a radiology finding including a feature depicted in the 3D image; extract at least one two-dimensional (2D) key image depicting the radiology finding from the 3D image; and embed or link the at least one extracted 2D key image with the radiology report.

In accordance with another aspect, a radiology workstation includes a computer connected to receive a stack of radiology images of a portion of a radiology examination subject. The computer includes at least one display component and at least one user input component. The computer includes at least one processor programmed to: display selected radiology images of the stack of radiology images on the at least one display component; receive entry of a current radiology report via the at least one user input component and display the entered radiology report on the at least display component; detect identification via the at least one user input component of a location on a displayed selected radiology image of the stack of radiology images; identify a radiology finding for the feature at the identified location by detecting textual description of the radiology finding in the radiology report; identify or extract at least one key image from the stack of radiology images depicting the radiology finding; and embed or link the at least one key image with the radiology report.

One advantage resides linking an image with an identified feature to a corresponding radiology report.

Another advantage resides in automatically saving identified images having the identified feature.

Another advantage resides in providing concurrent and optionally visually linked display of text of a radiology report and an image having an identified feature so as to reduce likelihood of error in transferring content from the image to the radiology report.

Further advantages of the present disclosure will be appreciated to those of ordinary skill in the art upon reading and understand the following detailed description. It will be appreciated that any given embodiment may achieve none, one, more, or all of the foregoing advantages and/or may achieve other advantages.

BRIEF DESCRIPTION OF THE DRAWINGS

The disclosure may take form in various components and arrangements of components, and in various steps and arrangements of steps. The drawings are only for purposes of illustrating the preferred embodiments and are not to be construed as limiting the disclosure.

DETAILED DESCRIPTION

In radiology reporting, the radiologist reviews a stack of 2D images (e.g., axial, sagittal, or coronal images in CT, MR, or SPECT). The radiologist can flip through images of the stack to identify an axial image that best captures a feature of interest, such as a tumor or lesion. Standard practice is that when a finding is made, for example a measurement of the size of the tumor or lesion, the radiologist may identify the key image in which the finding was observed/measured. This key image is stored with the radiology report as a reduced-resolution snapshot image, possibly with annotations such as labeling the tumor and/or showing the line along which the tumor measurement was made. In some radiology reporting systems the full-resolution DICOM image may also be hyperlinked with the key image, so that it can be easily pulled up when reviewing the report.

However, the radiologist has a short time interval to perform the reading, so that the key image selection may be cursory and the key image may not be ideal for making the finding.

A further difficulty is that radiologists conventionally review the images in their native format, such as the stack of axial slices. The radiologist may be concerned that a non-native format may introduce image artifacts. Time constraints also again come into play—a stack of N slices requires reviewing N images, whereas if the 3D image space is explored the number of potential images is infinite. However, the tumor may have its largest and/or smallest dimension in some oblique or non-axial plane.

Improved radiology workstation embodiments disclosed herein provide automated selection of the "best" key image, and optionally also automated generation of an optimized finding in that best key image. The key image selection module may be triggered automatically by detection via image processing of a tumor; or semi-manually by detecting a user interfacing operation such as using the cursor to define a tumor measurement line, or entry of the finding in the text of the report. The activated module searches the stack of axial slices for the best axial slice for illustrating the finding. In another embodiment, the full 3D space is searched for the best slice of any orientation. These embodiments are not mutually exclusive—in one embodiment the user is presented with two or three key images: a native axial slice for which the tumor has largest area; an interpolated oblique slice showing the largest tumor dimension; and optionally also an interpolated oblique slice showing the smallest tumor dimension. Optionally, the module also automatically performs the finding computation for each identified key image.

Various user interfacing approaches are contemplated. In a fully automated approach the image processing identifies one or more tumors and key image(s) for each tumor, and the user is presented with the key image and the proposed finding for each tumor in turn. In a semi-manual approach, upon detecting user entry of a finding, the key image selection module is invoked and identifies the best key image (and optionally the corresponding measurement) and proposes it to the radiologist.

The automated key image generation approaches disclosed herein can be extended to radiology findings other than tumor size findings, such as to lung texture findings indicative of emphysema, detecting calcifications in cardiac imaging, or so forth. For example, empirical feature selection and machine learning approaches can be used, i.e. a key image selector is trained on a set of labeled training imaging sets.

Illustrative embodiments automatically detect the most appropriate key image(s) corresponding to the finding description (based on the textual content in the report being created) to generate direct associations between report content and images. The detected image(s) can also be automatically added as a key image to PACS. To do so, the following discloses a radiology reporting support application module, for example implemented as a computer programmed to perform the disclosed operations, that automatically determines the radiology findings during report creation (for instance, during dictation) and automatically analyzes the image stack under review to determine the optimal key image that best describes the finding.

Figure 1:
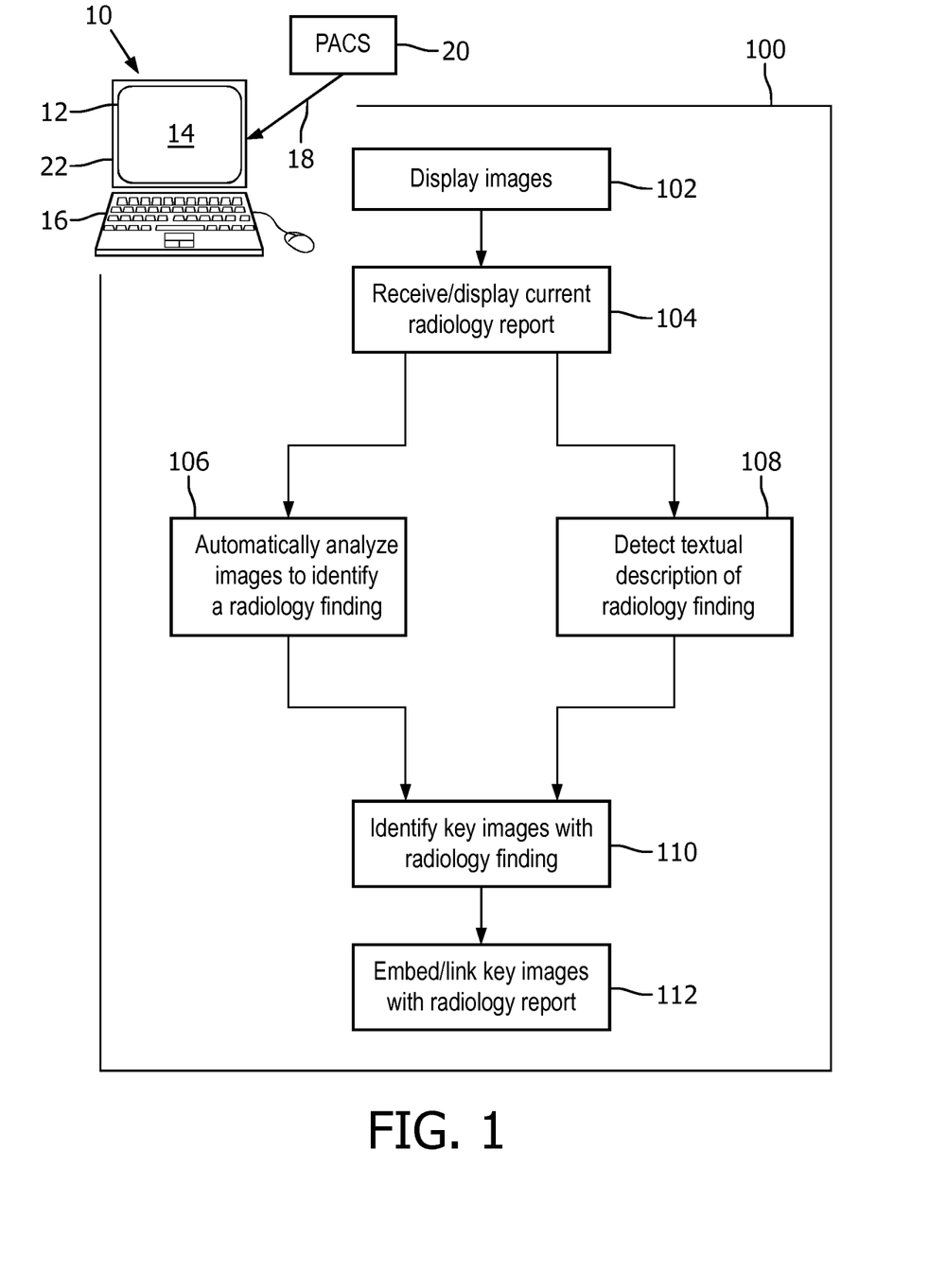
FIG. 1 shows a radiology workstation.

With reference to FIG. 1, an embodiment of a device for automatically detecting a key image is shown. As shown in FIG. 1, the device includes a radiology workstation 10, which may for example be implemented as a desktop computer, a "dumb" terminal connected with a network server, or any other suitable computing device. The workstation 10 includes a computer 12 with typical components, such as at least one display component 14, a user input component 16, a communication link 18, a database 20 such as a Picture Archiving and Communication System (PACS), and at least one processor 22 programmed to perform radiology reporting functions as disclosed herein. The at least one display 14 is configured to display one or more radiology images. For example, a selected image can be displayed on a first display, and the radiology report can be displayed on a second display. In some examples, the display 14 can be a touch-sensitive display. The user input component 16 is configured to select at least one of the images. In some cases, the user input component 16 can be a mouse, a keyboard, a stylus, and the like. In addition, the user input component 16 can be a microphone (i.e., to allow the user to dictate content to at least one of the radiology images), a headset, or simply be a user's finger (i.e., on a touch screen). The communication link 18 can be a wireless communication link (such as a wired or wireless Ethernet link, and/or a WiFi link), e.g. a hospital network enabling the radiology workstation 10 to retrieve a stack of radiology images making up a study from the PACS 20. In addition, the PACS or other database 20 is configured to store the stack of images, along with a plurality of radiology reports that include data entry fields indicative a type of the at least one target of interest. The at least one processor 22 is programmed to cause the radiology workstation 10 to perform an automatic key image detection method, as described in more detail below.

In some embodiments, the computer 12 is configured to receive a stack of radiology images of a portion (or all) of a radiology examination subject which are stored in the PACS 20. These images were previously uploaded to the PACS 20 from an imaging device (not shown) (e.g., a magnetic resonance device, an ultrasound device, a computer tomography device, a positron emission tomography device, a single-photon emission computed tomography device, and the like).

With continuing reference to FIG. 1, the at least one processor 22 of the workstation 10 is programmed to cause the workstation 10 to perform an automatic key image detection method 100. The method 100 includes: displaying selected radiology images of the stack of radiology images on the at least one display component 14 (102); receiving entry of a current radiology report via the at least one user input component 16 and displaying the entered radiology report on the at least display component (104); identify a radiology finding by at least one of (i) automated analysis of the stack of radiology images (106); and (ii) detecting textual description of the radiology finding in the current radiology report (108); identify or extract at least one key image from the stack of radiology images depicting the radiology finding (110); and embed or link the at least one key image with the current radiology report (112). In illustrative examples described herein, the identified feature is a tumor or a lesion. However, the identified feature may be any suitable tissues (e.g., healthy tissue, a cyst, other abnormalities, tissue texture, and the like).

At 102, selected radiology images of the stack of radiology images are displayed on the at least one display component 14. For example, the at least one processor 22 is configured to retrieve a selected image (not shown), either by receiving the images directly from an imaging device (not shown), or from the database 20 (not shown), and display it on the at least one display 14. In some examples, when multiple displays 14 are used, a first image can be displayed on a first display 14, and a second image can be displayed on a second display (not shown). In addition, the selected image can be displayed on the first display 14, and a radiology report retrieved from the database 20 can be displayed on the second display. The image(s) is selected by a user (i.e., a medical professional such as a physician, a nurse, a technician, and the like) of the workstation 10.

At 104, entry of a current radiology report is received via the at least one user input component 16, and the entered radiology report is displayed on the at least display component 14. In some examples, the radiology reports are also stored in the database 20, along with the images. The user may select at least one radiology report (e.g., by clicking on it or pointing to it with the user input component 16 (i.e., a mouse), by using text entry with the user input component 16 (i.e., a keyboard), or using dictation to select the radiology report with the user input component (i.e., a microphone), or may elect to create a new report, either ab initio or, more commonly, starting from a report template. Once the report is selected or created, the report (including content entered thus far) can be displayed on the display component 14 with the image (or on a separate display component).

Once the report and the selected images are displayed, a radiology finding is identified in the selected images. The at least one processor 22 is programmed to analyze a subset of the image stack (i.e., an interval of images around the slice being viewed at the moment by the radiologist) or the whole image stack. In one embodiment, at 106, the radiology finding is identified by an automated analysis of the stack of radiology images. To do so, the at least one processor 22 is programmed to convert the displayed stack of radiology images to a three-dimensional (3D) image. The at least one processor 22 is then programmed to automatically identify a feature depicted in the 3D image. For example, the at least one processor 22 is programmed to execute one or more image processing algorithms (e.g., segmentation, atlas-based analysis, etc.) to determine the most appropriate slice that match the findings determined through text analysis, as described in more detail below. In other examples, these automatic image processing algorithms for detection of the identified features can be prepared through machine learning algorithms and training-based algorithms using a database of training images with a known ground truth (e.g. radiology finding labels annotated to the images by skilled radiologists).

In another embodiment, at 108, the radiology finding is identified by detecting a textual description of the radiology finding in the radiology report. To do so, the at least one processor 22 is programmed to detect an identification via the at least one user input component 16 of a location on a displayed selected radiology image of the stack of radiology images. For example, the user can click on the displayed image (i.e., with the mouse) to identify a portion of the selected image (e.g., a dimension or axis of the region of interest), or use dictation (i.e., with the microphone) to identify a portion of the selected image (e.g., a dimension or axis of the region of interest). In one example, the user can click on the displayed image with the mouse to define a length along the image. The at least one processor 22 is then programmed to identify a feature at the identified location by automated analysis of the displayed selected radiology image of the stack of radiology images using the algorithms (e.g., segmentation, atlas-based analysis, etc.) described above. In this embodiment, the at least one processor 22 may convert the displayed stack of radiology images to a 3D image.

At 110, at least one key image is identified or extracted from the stack of radiology images depicting the radiology finding. The key image is identified as having a desired or target criterion of the region of interest. In one example, the radiology finding having desired or target criterion of the region of interest may constitute an identified feature in the selected image as having the largest cross-section. As a result, the image in stack of images that the at least one processor 22 determines to have an identified feature with the largest cross-section is considered to be a key image. In this example, more than one feature may be identified as having a larger cross-section relative to surrounding areas.

One difficulty with the approach of identifying the key image from the radiology images of the stack of radiology images is that the orientation of those "native" images may not be ideal for making or illustrating the finding. For example, if the imaging study acquired a stack of axial image slices and the finding is the long axis of a tumor, if the tumor is oriented such that its long axis does not lie in any axial plane then the finding cannot be effectively illustrated using the native (i.e. as-acquired) axial images.

In another example, which addressed the foregoing difficulty, the radiology finding having the desired or target criterion of the region of interest may constitute a maximum length of the identified feature along a long axis of the identified feature. In this example, the stack of radiology images is converted to a three-dimensional (3D) image. This can be done, for example, by treating the two orthogonal dimensions of the image slices as the x- and y-coordinates of an x-y-z Cartesian space. If the spacing between slices is known (this spacing is commonly stored as metadata annotated to the images or to the image study) then the z-coordinate is defined orthogonal to the slices with data points (voxels) spaced apart along the z-direction by the inter-slice spacing. In this embodiment, the at least one key image includes a key image extracted from the 3D image that contains the long axis of the identified radiology feature (i.e., the maximum length of the identified feature along a long axis of the identified feature). Because of the three-dimensionality of the 3D image, it is always possible to find a (possibly oblique) plane that contains the long axis using standard Euclidean geometry principles. As a result, the image in stack of images (or the 3D image) that the at least one processor 22 determines to have an identified feature with the maximum length of the identified feature along a long axis of the identified feature is considered to be a key image.

In a further example, the radiology finding having the desired or target criterion of the region of interest may constitute a minimum length of the identified feature along a short axis of the identified feature. In this example, the at least one key image includes a key image extracted from the 3D image that contains the short axis of the identified feature. As a result, the image in stack of images (or the 3D image) that the at least one processor 22 determines to have an identified feature a minimum length of the identified feature along a short axis of the identified feature is considered to be a key image. In this example, more than one feature may be identified as having a minimum length of the identified feature along a short axis of the identified feature relative to surrounding areas.

It will be appreciated that any suitable desired or target criterion of the region of interest can be used to identify one or more key images. As another example, an image corresponding to the mass centroid of the finding can be a key image. In some examples, a computational algorithm is used to determine the most specific body part and/or organ of the image where a measurement is made. Whenever a measurement is made on an image, this information is used to determine the body part and/or organ associated with this image (see Mabotuwana T, Qian Y, Determining scanned body part from DICOM study description for relevant prior study matching . . . , Stud Health Technol Inform., 2013; 192:67-71).

In yet another example, the radiology finding is identified by detecting textual description of the radiology finding in the radiology report. To do so, the at least one processor 22 is programmed to analyze the radiology report. For example, the at least one processor 22 is programmed to monitor the text of the radiology report being entered can to detect entry of key words corresponding to standard radiology findings, e.g. using Systematized Nomenclature of Medicine (SNOMED) terminology optionally augmented by additional shorthand and/or alternative terminology in common use by radiologists. To further improve the detection of findings, standard natural language processing (NLP) techniques can be used to extract findings in the current report. In this case, the at least one processor 22 is programmed to analyze the radiology report with an NLP engine to determine sections, paragraphs, and sentences. The sentences are then extracted and processed by an image-based finding extraction engine executed by the at least one processor 22. For instance, this engine will extract sentence "The left hepatic reference lesion measures approximately 6.4×5.4 cm".

Figure 2:
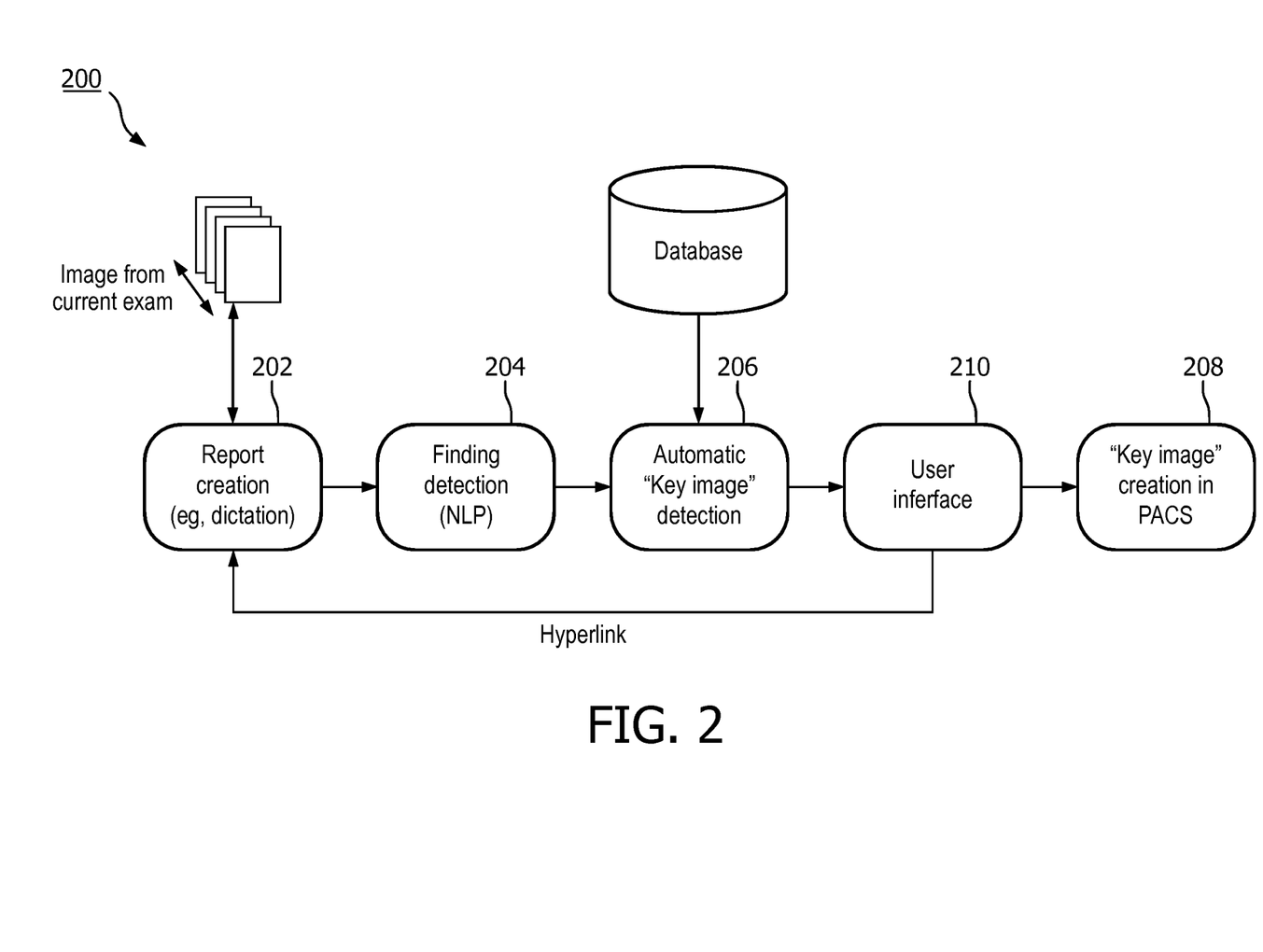
FIG. 2 shows a flowchart showing an exemplary method of use of the device of FIG. 1.

At 112, the at least one key image is embedded or linked with the radiology report. With reference to FIG. 2, and continuing reference to FIG. 1, the embedded or linking of the key image(s) to the radiology report is performed by a method 200 that is executed by the at least one processor 22. The method 200 includes: retrieving at least one radiology report (202); detecting a finding in the at least one radiology report (204); automatically detecting at least one key image that includes the detected finding (206); saving the detected key image to a database (208); and embedded or linking the detected finding in the at least one key image to the radiology report (210).

At 202, at least one radiology report is created or retrieved. As described above, the radiology reports can be created using a suitable report template, or a partially completed radiology report which is stored in the database 20 can be retrieved, along with the images. The user may create or select at least one radiology report (e.g., by clicking on it or pointing to it with the user input component 16 (i.e., a mouse), by using text entry with the user input component 16 (i.e., a keyboard), or using dictation to select the radiology report with the user input component (i.e., a microphone). Once the report is created or selected, it can be displayed on the display component 14 with the image (or on a separate display component), and the radiologist can enter text reporting on radiology findings into the report, e.g. using a keyboard or a dictation microphone with speech recognition software running on the computer.

At 204, a finding is detected in the at least one radiology report. As described above in reference to 110, the radiology finding is identified by detecting textual description of the radiology finding in the radiology report. To do so, the at least one processor 22 is programmed to analyze the radiology report. For example, the at least one processor 22 is programmed to use standard natural language processing (NLP) techniques to extract findings in the current report. In this case, the at least one processor 22 is programmed to analyze the radiology report with an NLP engine to determine sections, paragraphs, and sentences. The sentences are then extracted and processed by an image-based finding extraction engine executed by the at least one processor 22.

At 206, at least one key image that includes the detected finding is automatically detected. This process is described in more detail at 106, 108, and 110, described above.

At 208, the detected key images are saved to a database. In one example, the key images are saved to the database 20. In another example, the key images are saved to a PACS database (not shown). This can be performed using the communication link 18.

Figure 3:
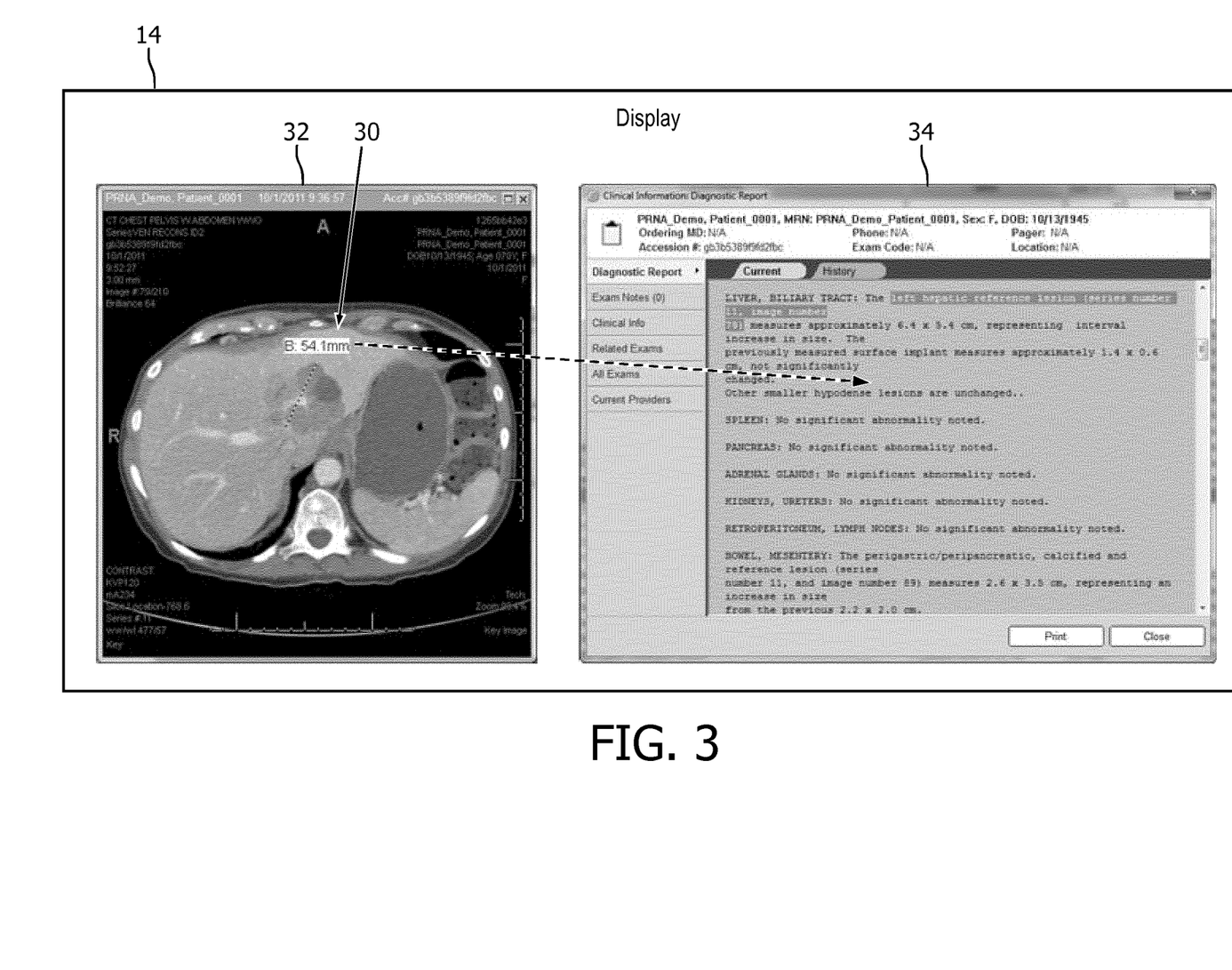
FIG. 3 shows an example operation of the device of FIG. 1.

At 210, the detected finding in the key images is embedded or linked to the radiology report. For example, the at least one processor 22 is programmed to automatically convert the key image information (e.g., coordinates, slice number, and the like) into text and automatically add this text to the report (for example in the form of a hyperlink). To do so, the at least one processor 22 is programmed to translate image information (such as slice number coordinates) for uniquely identifying the key image. The at least one processor 22 is then programmed to insert the converted text into the appropriate spot in the report. For example, the embedded text can be in the form of a hyperlink. By clicking on hyperlink, the corresponding image study is opened and the image slice corresponding to the key image is shown on the display component 14. In one example, the display component 14 is configured to populate the radiology report with the hyperlink containing the text content. As shown in FIG. 3, a hyperlink 30 containing the finding from a selected image 32 can be embedded into a radiology report 34 (shown by the dashed arrow in FIG. 3). The image 32 and the report 34 are displayed on the display component 14.

It will be appreciated that the various documents and graphical-user interface features described herein can be communicated to the various components 12, 14, 16, 18, 20, and data processing components 22 via a communication network (e.g., a wireless network, a local area network, a wide area network, a personal area network, BLUETOOTH®, and the like).

The various components 12, 14, 16, 18, 20, of the workstation 10 can include at least one microprocessor 22 programmed by firmware or software to perform the disclosed operations. In some embodiments, the microprocessor 22 is integral to the various components 12, 14, 16, 18, 20, so that the data processing is directly performed by the various components 12, 14, 16, 18, 20. In other embodiments the microprocessor 22 is separate from the various component v. The data processing components 22 of the device 10 may also be implemented as a non-transitory storage medium storing instructions readable and executable by a microprocessor (e.g. as described above) to implement the disclosed operations. The non-transitory storage medium may, for example, comprise a read-only memory (ROM), programmable read-only memory (PROM), flash memory, or other repository of firmware for the various components 12, 14, 16, 18, 20, and data processing components 22. Additionally or alternatively, the non-transitory storage medium may comprise a computer hard drive (suitable for computer-implemented embodiments), an optical disk (e.g. for installation on such a computer), a network server data storage (e.g. RAID array) from which the various component 12, 14, 16, 18, 20, data processing components 22, or a computer can download the device software or firmware via the Internet or another electronic data network, or so forth.

The disclosure has been described with reference to the preferred embodiments. Modifications and alterations may occur to others upon reading and understanding the preceding detailed description. It is intended that the disclosure be construed as including all such modifications and alterations insofar as they come within the scope of the appended claims or the equivalents thereof.

The invention claimed is:

1. A radiology workstation comprising:
   a computer connected to receive a stack of radiology images of a portion of a radiology examination subject, the computer including at least one display component and at least one user input component;
   wherein the computer includes at least one processor programmed to:
      display selected radiology images of the stack of radiology images on the at least one display component;
      receive entry of a current radiology report via the at least one user input component and display the entered radiology report on the at least one display component;
      identify a radiology finding at least by automated analysis of the stack of radiology images including converting the stack of radiology images to a three-dimensional (3D) image and identifying a feature depicted in the 3D image;
      extract at least one key image from the stack of radiology images depicting the radiology finding; and
      link the at least one key image with the radiology report;
      wherein the radiology finding includes a maximum length of the identified feature along a long axis of the identified feature, and the at least one key image includes a key image that contains the long axis of the identified feature and that is extracted from the 3D image.

2. The radiology workstation according to claim 1, wherein the radiology finding is identified by:
   detecting identification via the at least one user input component of a location on a displayed selected radiology image of the stack of radiology images; and
   identifying a feature at the identified location by automated analysis of the displayed selected radiology image of the stack of radiology images.

3. The radiology workstation according to claim 1, wherein the at least one key image includes a key image identified as the radiology image of the stack of radiology images for which the identified feature has largest cross-section.

4. The radiology workstation according to claim 1, wherein the identified feature is a tumor or lesion.

5. The radiology workstation according to claim 1, wherein the radiology finding is further identified by detecting textual description of the radiology finding in the radiology report.

6. A radiology workstation comprising:
   a computer connected to receive a stack of radiology images of a portion of a radiology examination subject, the computer including at least one display component and at least one user input component;
   wherein the computer includes at least one processor programmed to:
      display selected radiology images of the stack of radiology images on the at least one display component;
      receive entry of a current radiology report via the at least one user input component and displaying the entered radiology report on the at least one display component;
      convert the stack of radiology images to a three-dimensional (3D) image;
      identify a radiology finding at least by automated analysis of the 3D image;
      identify or extract at least one key image from the stack of radiology images depicting the radiology finding; and
      link the at least one key image with the radiology report;
   wherein the radiology finding includes a minimum length of the identified feature along a short axis of the identified feature, and the at least one key image includes a key image extracted from the 3D image that contains the short axis of the identified feature.

7. A radiology workstation comprising:
   a computer connected to receive a stack of radiology images of a portion of a radiology examination subject, the computer including at least one display component and at least one user input component;
   wherein the computer includes at least one processor programmed to:
      display selected radiology images of the stack of radiology images on the at least one display component;
      receive entry of a current radiology report via the at least one user input component and display the entered radiology report on the at least one display component;
      convert the stack of radiology images to a three-dimensional (3D) image;
      identify a radiology finding including a feature depicted in the 3D image at least by detecting textual description of the radiology finding in the radiology report;
      extract at least one two-dimensional (2D) key image depicting the radiology finding from the 3D image; and
      link the at least one extracted 2D key image with the radiology report;
   wherein the radiology finding includes a maximum length of the identified feature along a long axis of the identified feature, and the at least one 2D key image extracted from the 3D image includes a 2D key image extracted from the 3D image that contains the long axis of the identified feature.

8. The radiology workstation according to claim 7, wherein the at least one processor is further programmed to:
identify a key image as the radiology image of the stack of radiology images for which the identified feature has largest cross-section; and
embed or link the identified key image with the radiology report.

9. The radiology workstation according to claim 7, wherein the radiology finding includes a minimum length of the identified feature along a short axis of the identified feature, and the at least one 2D key image extracted from the 3D image includes a 2D key image extracted from the 3D image that contains the short axis of the identified feature.

10. The radiology workstation according to claim 7, wherein the identified feature is a tumor or lesion.

11. The radiology workstation according to claim 7, wherein the radiology finding is identified by automated analysis of the stack of radiology images and detecting textual description of the radiology finding in the radiology report.

12. The radiology workstation according to claim 7:
wherein the at least one processor is further programmed to:
detect identification via the at least one user input component of a location on a displayed selected radiology image of the stack of radiology images.

13. A radiology workstation comprising:
a computer connected to receive a stack of radiology images of a portion of a radiology examination subject, the computer including at least one display component and at least one user input component;
wherein the computer includes at least one processor programmed to:
display selected radiology images of the stack of radiology images on the at least one display component;
receive entry of a current radiology report via the at least one user input component and displaying the entered radiology report on the at least one display component;
identify a radiology finding including a feature by at least one of (i) automated analysis of the stack of radiology images and (ii) detecting textual description of the radiology finding in the radiology report;
identify or extract at least one key image from the stack of radiology images depicting the identified feature; and
embed or link the at least one key image with the radiology report,
wherein the radiology finding includes a maximum length of the identified feature along a long axis of the identified feature, and the at least one key image includes a key image that contains the long axis of the identified feature and that is extracted from a three-dimensional (3D) image generated by conversion of the stack of radiology images to said 3D image.

14. The radiology workstation of claim 13, wherein the identified feature is a tumor or a lesion or a cyst.

15. The radiology workstation of claim 13, wherein the radiology finding further includes a minimum length of the identified feature along a short axis of the identified feature, and the at least one key image further includes a key image extracted from the 3D image that contains the short axis of the identified feature.

* * * * *